United States Patent [19] [11] Patent Number: 4,727,328
Carper et al. [45] Date of Patent: Feb. 23, 1988

[54] PATIENT HANDLING ARRANGEMENTS FOR NMR IMAGING SYSTEMS

[75] Inventors: Robert L. Carper, Hudson; John T. Keller, Willoughby, both of Ohio

[73] Assignee: Technicare Corporation, Solon, Ohio

[21] Appl. No.: 798,262

[22] Filed: Nov. 15, 1985

[51] Int. Cl.⁴ .............................................. G01R 33/20
[52] U.S. Cl. .................................. 324/318; 378/209; 128/653
[58] Field of Search ............... 324/318, 309, 300, 322, 324/307; 128/653; 378/208, 209

[56] References Cited

U.S. PATENT DOCUMENTS 4,131,802 12/1978 Braden et al. ...................... 378/208
4,452,439 6/1984 Hogan ................................. 378/209
4,567,894 2/1986 Bergman ............................. 128/653
4,629,989 12/1986 Riehl et al. ........................ 324/318

Primary Examiner—Stewart J. Levy
Assistant Examiner—Louis M. Arana
Attorney, Agent, or Firm—W. Brinton Yorks, Jr.

[57] ABSTRACT

A patient handling system for an NMR imaging system includes a portable patient table having a bottom portion and a top portion. The table is docked adjacent to the magnet of an NMR system. The top portion may be elevated to align the top portion with the magnet bore. A patient pallet, located on the top portion of the table, is then moved into and out of the magnet bore. The pallet includes a number of modules upon which the patient reclines. At least one module includes a radio frequency coil for NMR imaging. The other modules are dummy modules which do not contain r.f. coils and support other parts of the patients's body.

13 Claims, 11 Drawing Figures

PATIENT HANDLING ARRANGEMENTS FOR NMR IMAGING SYSTEMS

This invention relates to nuclear magnetic resonance (NMR) imaging systems and, in particular, to patient handling systems for NMR diagnostic imaging of patients.

NMR imaging systems are in current use for performing medical diagnostic imaging of human patients. In such systems the patient is located in the bore of a large resistive or superconducting magnet. The magnet produces a generally homogeneous magnetic field in the magnet bore. The bore hole is surrounded by gradient coils and at least one radio frequency (r.f.) coil The r.f. coil is used to excite resonant nuclei in the patient's body and may also be used to receive the resultant NMR signals. The gradient coils are activated to spatially encode the magnetic field and hence the nuclei at different positions in the body.

During imaging the patient is reclining in a prone position in the horizontal magnet bore. The patient does not crawl into the bore, but generally reclines on a patient pallet located outside the magnet. The patient and pallet are then rolled into the magnet with the patient positioned so that the body region to be imaged is in a predetermined relationship to the r.f. and gradient coils.

However, many patients undergoing NMR diagnostic imaging are critically ill, and are not sufficiently ambulatory so that they can climb onto and off of the patient pallet. Hence it is desirable for the pallet arrangement to facilitate the handling of critically ill patients who are not ambulatory.

The NMR imaging system should be designed so that the imaging procedure can be interrupted and the patient quickly removed from the magnet in the event of a medical emergency. It should be possible to remove the patient from the magnet bore in a matter of seconds so that a patient experiencing a medical emergency can be immediately attended to by medical personnel. Quick retrieval from the magnet bore must be possible even in the event of a power outage which could completely shut down all electrical systems of the NMR imaging equipment.

In NMR diagnostic imaging the r.f. coil which surrounds the patient can be used to gather NMR signal information from the entire body. This coil may be used to provide cross-sectional images of the whole body. However, it is often desirable to use smaller, more specialized r.f. coils to provide detailed images of specific areas of the body. Known r.f. coils for such specialized purposes include head coils, breast coils, and surface or spine coils. These coils can be used for both r.f. excitation signal transmission and NMR signal reception. They may also be used only as reception coils, with r.f. signal transmission being performed by the r.f. coil which surrounds the body.

The specific nature of these coils require that they be placed in close proximity to the specific body region which is to be imaged. Head coils must be placed about the head, breast coils around the breasts, and so forth. Because the size of the patient will vary from one person to another, it must be possible to locate the coils so that they accommodate the anatomy of the patient. Moreover, surface coils may be used for numerous applications. When placed at the lower back area a surface coil can be used to image the base of the spine or the kidneys. When located higher on the body they can image the upper spine and neck or the lungs. It is desirable to be able to easily move and connect these specialized coils prior to imaging, and for the coils to afford a maximal amount of patient comfort.

In accordance with the principles of the present invention, a patient handling system is provided for an NMR imaging system. The patient handling system includes a patient table comprising a base and a pallet. The base has a bottom portion which is wheel mounted and includes electronics and motors. The top portion of the base supports the pallet and is powered to move up and down. The top portion may be lowered while medical personnel ease a helpless patient onto the pallet. The patient table is then wheeled to the NMR magnet where it docks with the magnet housing at the bore opening. The top portion is then mechanically elevated so that the pallet is aligned at the level of the magnet bore. Since different magnets may be mounted at different floor elevations, the vertically travelling top portion of the patient table can accommodate NMR magnets of various bore elevations.

The pallet includes a tray and a set of modules. The tray is concave and has wheels along its two lateral edges. The tray rides on the wheels as it moves into and out of the magnet bore. At the end of the pallet which opposes the magnet bore is a mechanically activated latch. The latch engages a pin on the mechanism which drives the pallet into and out of the magnet.

The modules are concave-shaped plastic molded pieces of two varieties. Some of the modules are active coil modules which contain various ones of the specialized r.f. coils. Others are dummy modules of various lengths with the same concave surfaces as ones of the active modules. Flanges on the sides of the modules rest on the lateral edges of the pallet when the modules are placed in the concave pallet. The active and dummy modules can be placed in arbitrary sequences within the pallet so that the active coil module is adjacent the part of the body which is to be imaged, and the dummy modules complete the concave surface which supports the remainder of the patient's body. For instance, a head coil module can be placed at one end of the pallet, and one or more dummy modules used to fill out the rest of the patient to support the body of the patient. If the lower back is to be imaged, dummy modules are placed in the pallet to support the head and upper trunk of the patient and to support the buttocks and legs. An active surface coil or spin coil module is placed between the dummy modules and located adjacent to the lower back area of the patient.

Figure 1:
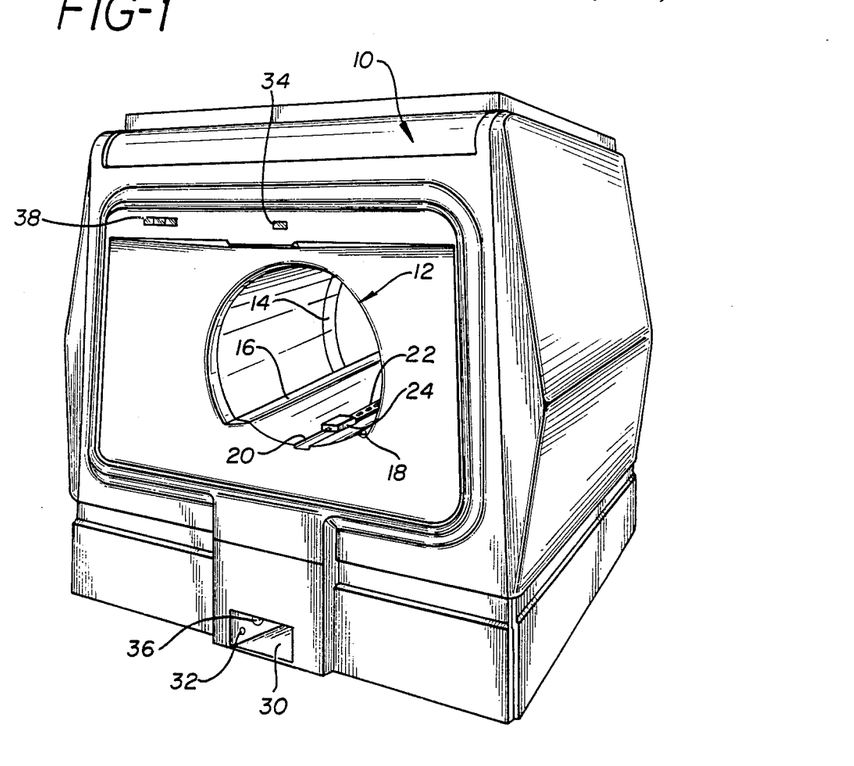
FIG. 1 illustrates a magnet for a whole body NMR imaging system.

Referring to FIG. 1, a magnet for an NMR imaging system for use with the patient handling system of the present invention is shown. The magnet is completely enclosed in a magnet housing 10 made of a plastic or other non-ferrous material. Located in the center of the magnet and housing 10 is the magnet bore 12. The magnet bore is about 100 centimeters in diameter. Fitted within the magnet bore and partially visible in FIG. 1 is an r.f. body coil 14, with an inside diameter of about 55 centimeters. Not visible in FIG. 1 are the gradient coils of the system, which surround the tube that forms the inner surface of the magnet bore.

The bottom of the magnet bore is concave, with rails 16, 18 running through the opening. The wheels of the pallet ride on these rails as the pallet moves through the magnet bore.

Figure 2:
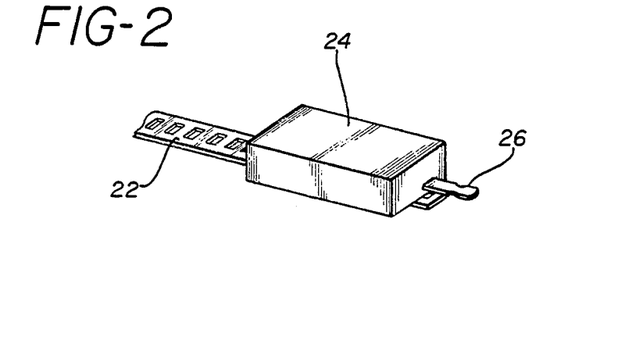
FIG. 2 is a detailed illustration of a latch mechanism for moving a pallet in the magnet.

At the bottom center of the magnet bore is a groove 20. Two perforated belts made of nylon, delron or similar plastic materials move through this groove. Since the belts overlap, only the upper drive belt 22 is visible in the FIGURE. Located near the end of the belt 22 is a nylon latchpin block 24 with a latchpin 26 extending therefrom. The belt, block and latchpin are shown in greater detail in FIG. 2. The plastic belt winds and unwinds from a mechanically driven drive belt reel located at the far end of the bore and not visible in this FIGURE. As the belt moves through the groove 20, it carries the latchpin block with it. The latchpin mates with a latch on the pallet, and the plastic belt is strong and rigid enough to push and pull the pallet with a 400 pound patient on it into and out of the magnet bore.

The second belt which rides in the groove 20 beneath the drive belt 22 is an identical perforated belt used for position sensing. As the position sensing belt winds and unwinds from its reel at the back of the magnet in unison with the drive belt, the perforations of the position sensing belt engage a toothed gear on a shaft with a shaft encoder. The shaft encoder provides a signal indicative of the distance of travel of the two belts, and hence the position of the pallet and patient. The position signal is processed and displayed on a numeric display 38 on the front of the magnet housing to inform the operator of the position of the patient with respect to the gradient and r.f. body coils. The position sensing system has been found to accurately display the patient position to within ±0.2 centimeters.

The nylon or delron belt has been found to be preferable to a chain drive arrangement. The belt is rigid and tough enough to drive the pallet and patient, and does not pose an eddy current or field inhomogeneity problem, as would a steel drive chain.

Located at the bottom of the front of magnet housing 10 is an opening 30 for the mating mechanism which joins with the patient table. When the patient table is aligned with the front of the magnet housing, two arms swing out from the patient table and into the opening 30. When the patient table is properly docked, the arms from the table close two interlock switches 32. The closed switches activate an indicator lamp 34 on the magnet housing, informing the operator that the patient table has properly docked with the magnet. The outward swinging arms also connect a power plut into a mating socket 36 in the opening 30. A power supply in the magnet housing is connected to the socket 36 to continuously charge the battery in the patient table. This battery charging connector is the only electrical connection between the magnet housing and magnet and the patient table.

Figure 3:
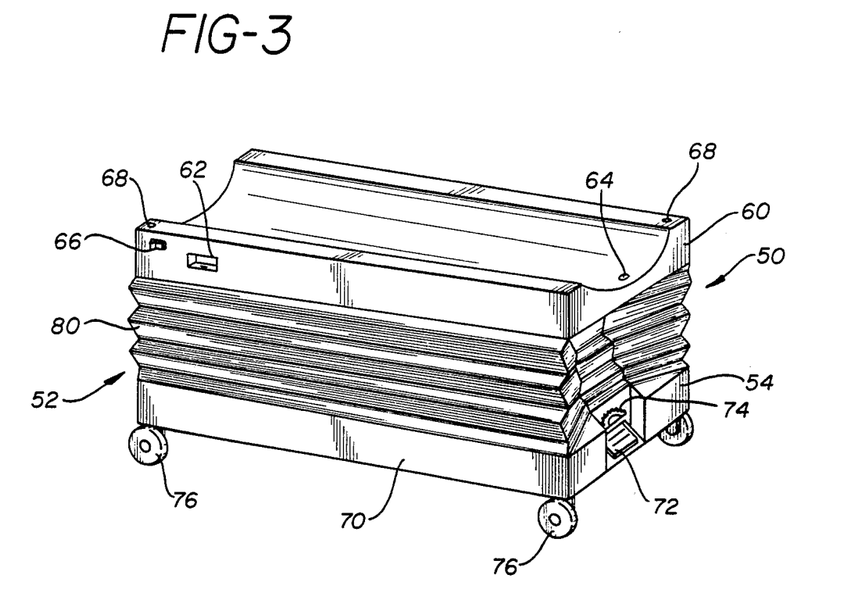
FIG. 3 illustrates a patient table for an NMR imaging system constructed in accordance with the principles of the present invention.

FIG. 3 shows a patient table base 50 constructed in accordance with the principles of the present invention. The base 50 includes a top portion 60 and a bottom portion 70. The two portions are jointed by an accordioned shroud 80, which compresses and unfolds as the top portion is moved up and down. The operator elevates the top portion by pressing on the switches located in two indentations 62, located on opposite sides of the top portion 60. When the operator presses on the lower interior surface of the indentation, a switch is closed to lower the top portion. When the operator presses on the upper interior surface of the indentation, the top portion moves up. Releasing the switches stops the top portion at its then current elevation.

A pallet sensing switch 64 is located at one end of the top portion 60. The pallet closes this switch when it is fully positioned on the top portion 60. Unless this switch is closed, signalling that the pallet is in its home position, the patient table cannot be undocked from the magnet housing. This prevents the patient table from being undocked and moved away from the magnet housing until the patient and pallet are safely located on the top portion of the patient table.

The end of the patient table which docks with the magnet housing is indicated at 52. At the other end 54 of the table are located a foot-operated brake pedal 72 and a manual undocking ratchet 74. The brake pedal is pivoted about its horizontal center such that pressing on the top of the pedal locks the wheels 76 so that the table cannot be moved. Pressing on the bottom of the pedal releases the wheels.

Figure 4:
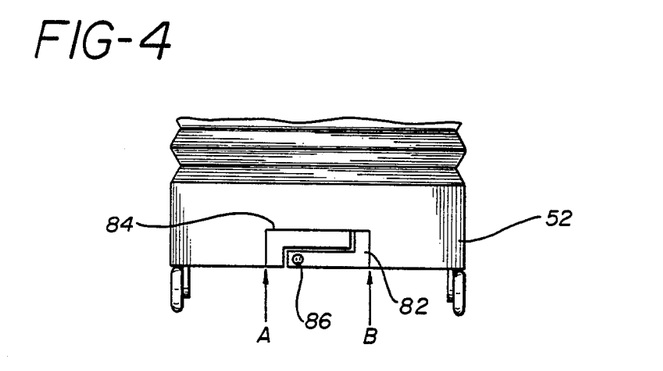
FIG. 4 is a partial end view showing the docking mechanism of the patient table.

FIG. 4 illustrates end 52 of the bottom portion 70 and the docking mechanism. Two arms 82 and 84 are normally folded in flush with the surface of end 52 when the table is being moved. There is thus no hazard posed by any extensions from the table. When the table is rolled up to the magnet housing in a position for docking, one of the docking switches 66 on the top portion is depressed. The docking arms 82 and 84 then pivot outward from the table, pivoting about pivot points A and B. The pivoting arms swing into the opening 30 of the magnet housing and press interlock switches 32 closed. The electrical socket 86 on the arm 82 engages its mating connector 36 in opening 30 to provide charging current for the patient table battery.

Figure 5:
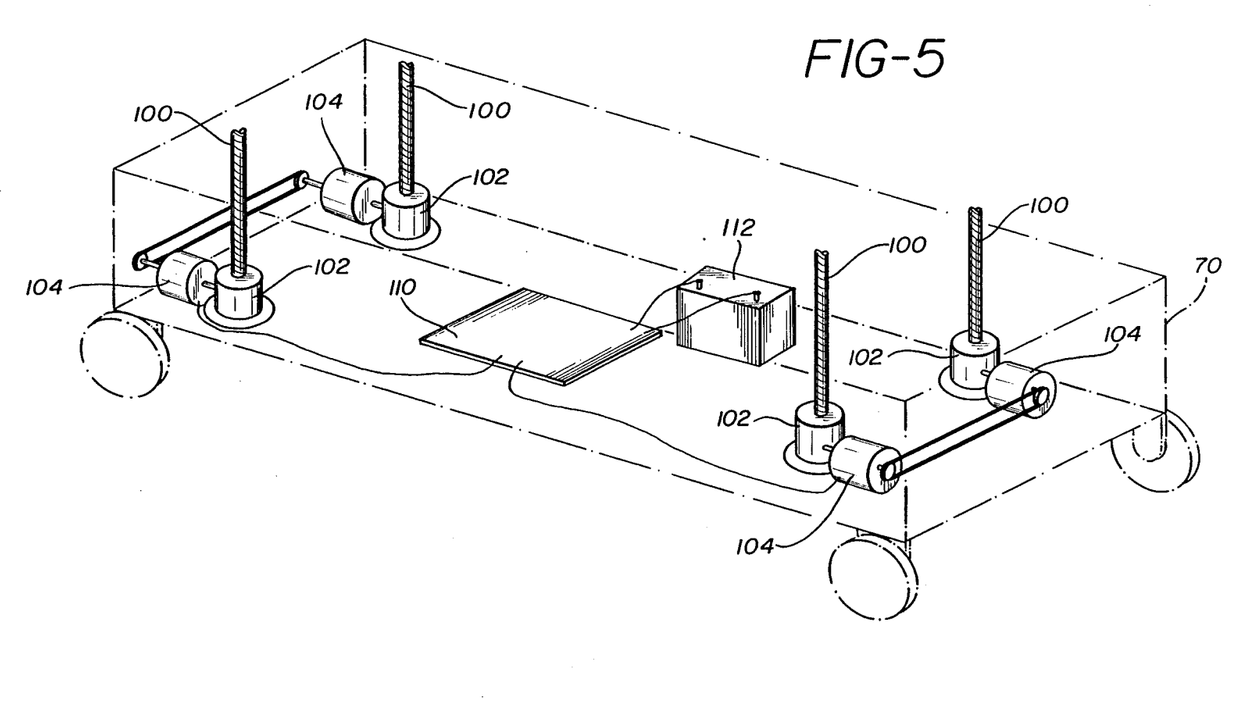
FIG. 5 illustrates the elevation drive mechanism of the patient table.

The breakaway illustration of the bottom portion 70 in FIG. 5 shows some of the components housed in the bottom portion. Four threaded rods 100 extend up from the bottom portion and into threaded fittings in the top portion 60. The rods 100 are mounted on gearboxes 102, driven by motors 104. As the motors and gearboxes turn the rods, the top portion moves up and down over a range of travel of about eleven inches from about twenty-six inches in elevation to about thirty-seven and one-half inches. The motor pairs at each end of the table are connected by belt and pulley arrangements to ensure that the motors at each end operate in unison. Shaft encoders of a motor at each end are wired to a processing board 110. Signals from the shaft encoders are monitored by the board electronics to ensure that the two ends of the tables are moving in unison. Thus, the top portion will always be kept in a horizontal position as it is moving up and down. A failure of any motor will be sensed by circuitry on board 110, which will shut down all the motors. The circuitry and motors of the table are powered by a battery 112, which is charged while the table is docked as explained above.

Figure 6:
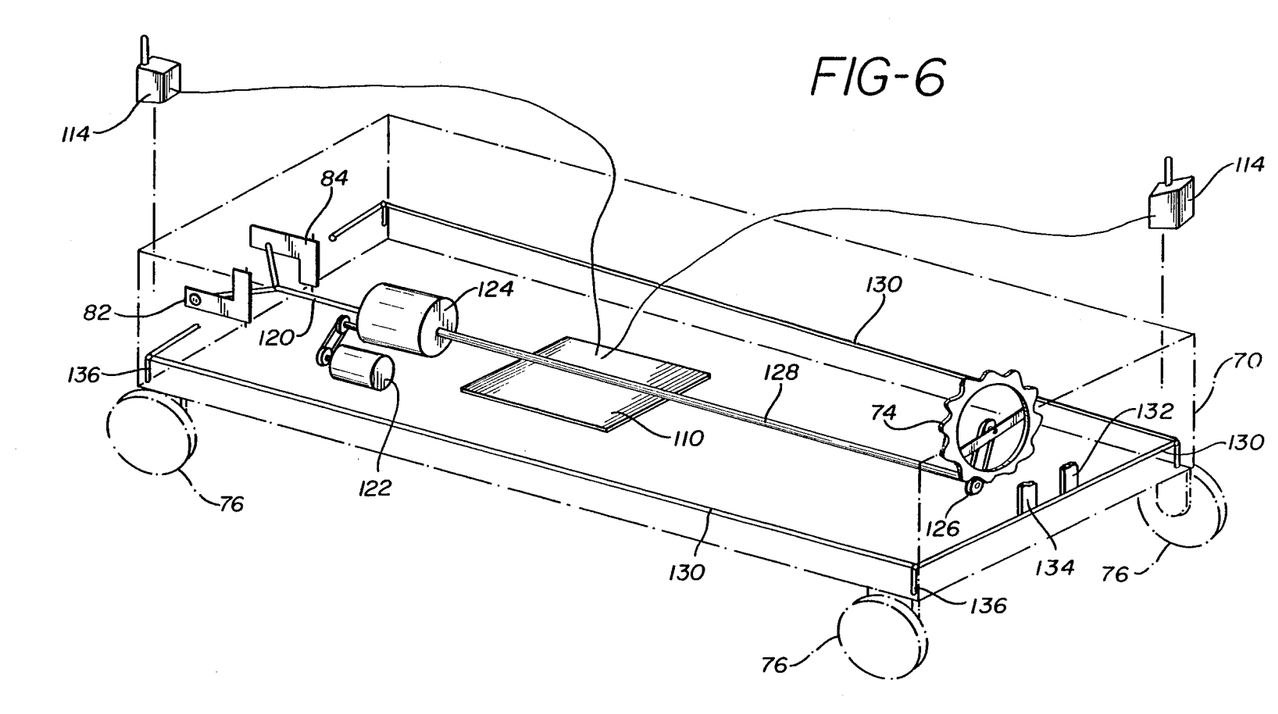
FIG. 6 illustrates details of the patient table docking mechanism and pallet locking mechanism.

FIG. 6 shows other components of the patient table. A motor 122 is activated by rocker switches 66 on the top portion of the table to dock and undock the table. The motor 122 is connected to a gearbox 124, which extends and retracts a mechanical linkage 120 to pivot the docking arms 82 and 84. In the event of a power failure in the table, the ratchet 74 is turned by hand to undock the table. Turning the ratchet turns rod 128 by a belt drive arrangement 126, which mechanically and manually undocks the patient table.

As mentioned above, the patient table cannot be undocked until the pallet is located in full position on the top portion of the patient table. When the pallet is in this position, holes in the pallet table are aligned with holes 68 on the top portion and shown in FIG. 3. When undocking is initiated, linearly driven plungers 114 are activated to protrude through holes 68 and into the aligned holes in the pallet, thereby holding the pallet securely in place on the patient table. The plungers 114 retract as the table is docked with the magnet. In the event of a power failure the plungers may be manually extended and retracted.

Also shown in FIG. 6 are rods 132 and 134, which are connected to and move up and down with the brake pedal 72. When the rods are pushed down they in turn push down bars 130, which press vertical rods 136 against the outer circumference of the wheels 76 for braking.

Figure 7:
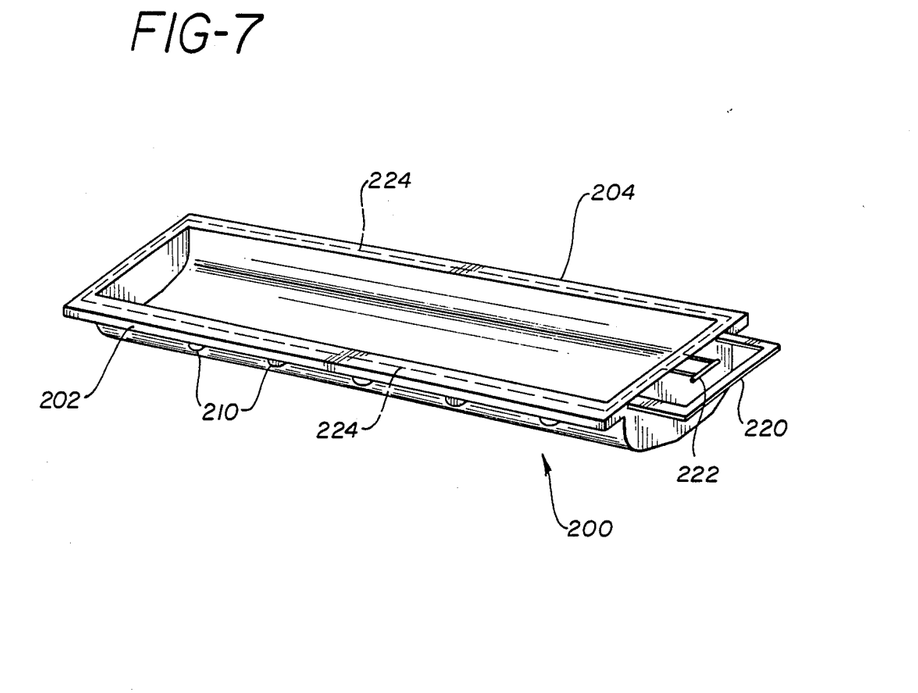
FIG. 7 illustrates a patient pallet.
Figure 8:
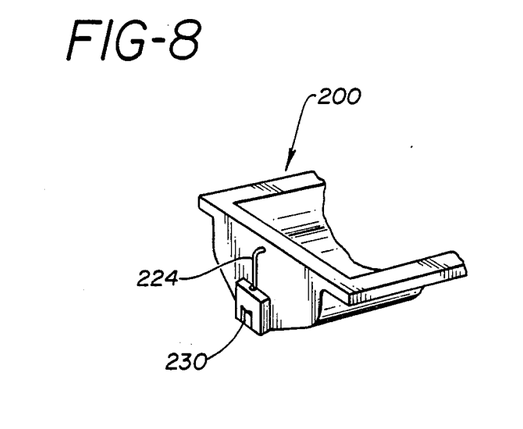
FIG. 8 illustrates the drive mechanism latch of the patient pallet.

FIG. 7 shows a pallet 200. The concave pallet has flanges 202 and 204 extending outward from the sides of the pallet. Wheels 210 are located along the bottom of each flange and ride on the magnet housing rails 16 and 18 and the aligned upper surfaces of the top portion of the table. At one end of the pallet is an emergency release handle 220. In the event it becomes necessary to quickly remove a patient from the magnet, the operator grasps the handle and squeezes bar 222 toward the handle 220. Bar 222 connects to a mechanical linkage 224 located inside the upper flange and ends of the pallet, as indicated by lines 224. The linkage 224 connects to the drive mechanism latch 230, which is shown in FIG. 8. When linkage 224 is activated it mechanically opens latch 230. releasing latchpin 26 to disconnect the pallet from the pallet drive mechanism. The pallet can then be swiftly rolled manually out of the magnet bore by pulling it by the handle 220.

Typical modules for the pallet 200 which contain r.f. coils are shown and described in U.S. patent application Ser. No. 642,613, which is hereby incorporated by reference. The active modules there shown, including a surface coil module 250 and a head coil module 260, are reproduced as FIGS. 9 and 10 of this application. Each module has flanged surfaces 262, and an intermediate curved surface 254 which accommodates the patient. In constructed embodiments each module is nineteen inches wide and the standard concave surface contour has a fifteen inch radius. The length depends upon the type of coil. The head coil modules of FIG. 10 is seen to have a lesser concave radius than the standard curvature of the surface coil in order to bring the coil 256 into closer proximity to the head of the patient.

Figure 9:
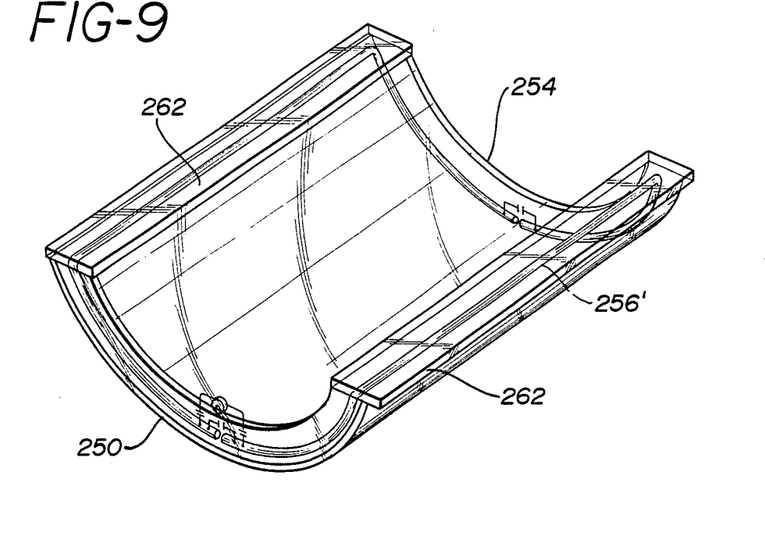
FIG. 9 illustrates a surface coil module.
Figure 10:
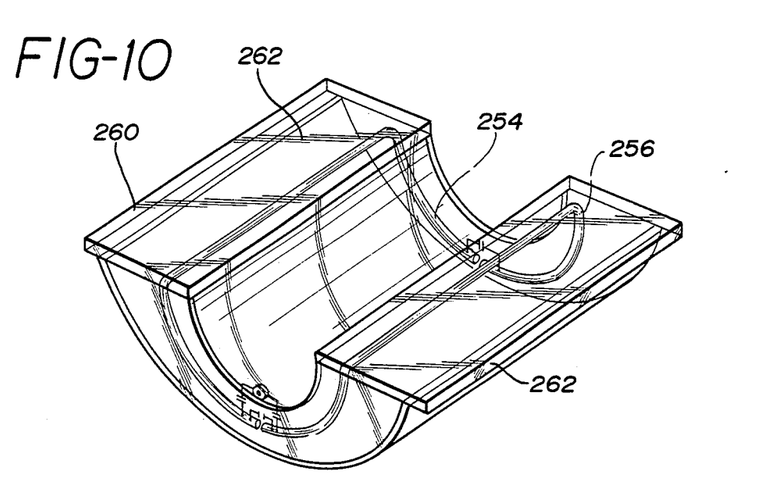
FIG. 10 illustrates a head coil module.
Figure 11:
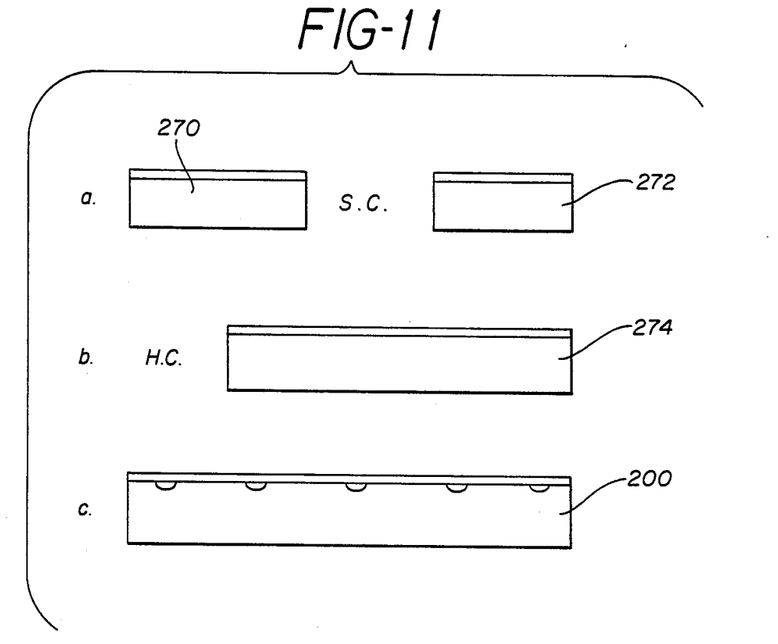
FIG. 11 illustrates various configurations of active coil modules and dummy modules for the patient pallet.

The dummy modules are configured with the same dimensions and radius of curvature as those of the surface coil module of FIG. 9. These modules, however, contain no coils or other components, hence the name dummy module. The dummy modules are produced in various lengths so as to intermix with the active coil modules in various configurations. For example, FIG. 11c illustrates the pallet 200 in a side view. Aligned above the pallet 200 are two possible module configurations. To image the lower back, a dummy module 270 would be placed in the pallet 200 to support the patient's head and shoulders. A dummy module 272 would be placed at the other end of the pallet to support the buttocks and legs. Between them in the pallet would be the surface coil module 250, as indicated by S.C. between the dummy modules of FIG. 11a.

To use the head coil module 260 to image the head, the head coil module would be placed in the pallet 200 at one end as indicated by H.C. in FIG. 11b. The rest of the pallet could be filled in by one large dummy module 274 to support the patient's entire body. Alternately, of course, several smaller modules could be used.

What is claimed is:

1. In a nuclear magnetic resonance imaging system, including a magnet housing containing a magnet having a bore in which a subject to be imaged is to be located, a patient handling system comprising:
   a mobile patient table which may be located so as to oppose said magnet bore, said patient table including a bottom portion and a top portion;
   a patient pallet, movably located on said top portion and adapted to be moved between said top portion and said magnet bore; and
   docking means for mating said mobile patient table with said magnet, said docking means providing an electrical connection between said magnet housing and said patient table.

2. The nuclear magnetic resonance imaging system of claim 1, wherein said mobile patient table includes means for elevating said top portion relative to said bottom portion, and wherein said electrical connection provided by said docking means energizes said elevating means.

3. In a nuclear magnetic resonance imaging system, including a magnet having a bore in which a subject to be imaged is to be located, a patient handling system comprising:
   a patient table which may be located so as to oppose said magnet bore, said patient table including a bottom portion and a top portion;
   a patient pallet, movably located on said top portion and adapted to be moved between said top portion and said magnet bore;
   mechanically driven transport means for transporting said patient pallet into and out of said magnet bore, including latch means for connecting said transport means to said patient pallet; and
   release means, located on said pallet, for manually releasing said latch means from said pallet, whereby said pallet may be manually removed from said magnet bore.

4. The nuclear magnetic resonance imaging system of claim 3, wherein said release means comprises a handle suitable for manually moving said pallet.

5. The nuclear magnetic resonance imaging system of claim 4, wherein said latch means engages said pallet proximate one end of said pallet, and said release means is located proximate the opposite end of said pallet.

6. The nuclear magnetic resonance imaging system of claim 3, wherein said transport means includes plastic belt means which is mechanically driven for moving said pallet into and out of said magnet bore.

7. The nuclear magnetic resonance imaging system of claim 6, wherein said plastic belt means is perforated, and further comprising means for indicating the position of said pallet within said magnet bore, said indicating means including a toothed gear tracking the perforations of said plastic belt means.

8. In a nuclear magnetic resonance imaging system, including a magnet having a bore in which a subject to be imaged is to be located, a patient handling system comprising:
   a mobile patient table which may be located so as to oppose said magnet bore, said patient table including a bottom portion and a top portion;
   a patient pallet, movably located on said top portion and adapted to be moved between said top portion and said magnet bore;
   docking means for mating said mobile patient table with said magnet; and
   retaining means for preventing movement of said patient pallet relative to said top portion when said mobile patient table is not mated with said magnet.

9. The nuclear magnetic resonance imaging system of claim 8, wherein said docking means includes means for enabling the release of said retaining means to permit said patient pallet to be moved into said magnet bore when said mobile patient table is properly mated with said magnet.

10. The nuclear magnetic resonance imaging system of claim 9, wherein said retaining means comprises linearly driven plungers extendable through holes in said top portion and said patient pallet.

11. The nuclear magnetic resonance imaging system of claim 8, wherein said top portion includes sensor means for sensing the safe positioning of said patient pallet on said top portion.

12. The nuclear magnetic resonance imaging system of claim 11, wherein said docking means is inhibited by said sensor means from undocking said mobile patient table and said magnet unless said patient pallet is safely positioned on said top portion.

13. In a nuclear magnetic resonance imaging system, a patient pallet comprising a plurality of modules for supporting a subject, said modules being capable of being aligned to form a substantially uniform supporting surface over a majority of its surface area, and including at least one active coil module including a radio frequency coil, and at least one dummy module similar to said active coil module and containing no radio frequency coil.

* * * * *